(12) United States Patent
Grøndahl et al.

(10) Patent No.: US 6,585,982 B1
(45) Date of Patent: *Jul. 1, 2003

(54) TREATMENT OF INFERTILITY

(75) Inventors: Christian Grøndahl, Vaerlose (DK); Thomas Høst Hansen, Copenhagen (DK); Alexander Rübig, Berlin (DE); Christa Hegele-Hartung, Mulheim/Ruhr (DE)

(73) Assignee: NNA/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/528,610

(22) Filed: Mar. 20, 2000

Related U.S. Application Data

(63) Continuation of application No. PCT/DK00/00074, filed on Feb. 23, 2000.
(60) Provisional application No. 60/130,816, filed on Apr. 23, 1999.

(30) Foreign Application Priority Data

Feb. 24, 1999 (DK) .......................................... 1999 00255
Sep. 16, 1999 (DK) .......................................... 1999 01310

(51) Int. Cl.$^7$ ............................ A61K 9/00; A61K 39/00
(52) U.S. Cl. ................. 424/400; 424/184.1; 424/185.1; 424/193.1
(58) Field of Search ............................... 424/400, 184.1, 424/185.1, 193.1; 514/15, 2

(56) References Cited

U.S. PATENT DOCUMENTS 6,281,013 B1 * 8/2001 Grondahl .................... 435/363

FOREIGN PATENT DOCUMENTS

| WO | WO 94/19455 | 9/1994 |
|----|-------------|--------|
| WO | WO 96/00235 | 1/1996 |
| WO | WO 96/27658 | 9/1996 |
| WO | WO 97/00883 | 1/1997 |
| WO | WO-97/00883 | * 1/1997 |
| WO | WO 97/00884 | 1/1997 |
| WO | WO 98/28323 | 7/1998 |
| WO | WO 98/54965 | 12/1998 |
| WO | WO 98/55498 | 12/1998 |

OTHER PUBLICATIONS

Smitz et al., Human Reproduction, vol. 14, pp. 145–161 (1999).

* cited by examiner

*Primary Examiner*—James M. Spear
*Assistant Examiner*—Blessing Fubara
(74) *Attorney, Agent, or Firm*—Richard W. Bork, Esq.; Reza Green, Esq.; Mark A. Began, Esq.

(57) ABSTRACT

In vitro fertilization can be improved by adding a meiosis activating compound.

15 Claims, No Drawings

TREATMENT OF INFERTILITY

CROSS-REFERENCE TO RELATED APPLICATIONS

This application is a continuation of PCT/DK00/00074 filed on Feb. 23, 2000 and claims priority under 35 U.S.C. 119 of Danish application no. PA 1999 00255 filed on Feb. 24, 1999, U.S. provisional application No. 60/130,816 filed on Apr. 23, 1999, and Danish application no. PA 1999 01310 filed on Sep. 16, 1999, the contents of which are fully incorporated herein by reference.

FIELD OF THIS INVENTION

This invention relates to an improved method of in vitro fertilisation (hereinafter designated IVF).

BACKGROUND OF THIS INVENTION

Since the first IVF pregnancy was delivered in 1978, this procedure has resulted in thousands of pregnancies and opened a vast new frontier of research and treatment for the infertile couples. Still, there is a significant need for improved infertility treatment modalities today. It is presumed that about one out of seven couples experience problems with subfertility or infertility.

IVF of human oocytes has become commonly used for the treatment of female and male subfertility. The standard IVF treatment includes a long phase of hormone stimulation of the female patient, e.g. 30 days, which is initiated by suppressing the patient's own follicle stimulating hormone (hereinafter designated FSH) and luteinising hormone (hereinafter designated LH) by gonadotropin releasing hormone (hereinafter designated GnRH), and this is followed by injections of exogenous gonadotropins, e.g. FSH and/or LH, in order to ensure development of multiple preovulatory follicles and aspiration of multiple in vivo matured oocytes immediately before ovulation. The aspirated oocyte is subsequently fertilised in vitro and cultured, typically for three days before transferral back into the uterus at the 4–8 cell stage. Continuous efforts have been made to optimise and simplify this procedure. Nevertheless, the overall pregnancy rate cannot be increased significantly over about 20% with the current treatment modalities. In a large European survey of IVF patients, it was found that 7.2 oocytes out of 11.5 aspirated oocytes per patient had undergone resumption of meiosis immediately before fertilisation, only 4.3 oocytes were fertilised and only 2.2 oocytes reached the 8-cell embryo stage after fertilisation and in vitro culture (ESHRE, Edinburgh, 1997).

Due to the very unpredictable quality of the state of the art embryos today, more than one embryo has to be transferred just to give a reasonable chance of success. Therefore, it is common to transfer 2–3 embryos (up to 5 embryos in some countries), which carries the very large side effect of multiple pregnancies with great discomfort and risk to both patient and children. Moreover, it has been estimated that the increased health care expenses due to multiple birth (twins, triplets etc.) is exceeding the entire IVF expenses.

Hence, there are several disadvantages with the current treatment, the four most notable being:

1. the risk of ovarian hyperstimulation with injecting gonadotropins which is a potential fatal condition that requires hospitalisation,
2. multiple pregnancies (50–1.000 times the normal frequency of twins and triplets, respectively),
3. the existence of considerable patient segments that do not tolerate the current method due to, e.g. polycystic ovarian syndrome and many diabetics,
4. a potential long-term cancer risk.

Furthermore, weight gain, bloating, nausea, vomiting, labile mood and other patient discomforts together with patient reluctance to inject themselves are reported as disadvantages.

It is known from WO 96/00235, corresponding to U.S. Pat. No. 5,716,777, that certain sterol derivatives can be used for regulating meiosis. An examples of such a sterol is 4,4-dimethyl-5α-cholesta-8,14,24-triene-3β-ol (hereinafter designated FF-MAS).

Herein, the term MAS compounds designates compounds which mediate the meiosis of oocytes. More specifically, MAS compounds are compounds which in the test described in Example 1 below has a percentage germinal vesicle breakdown (hereinafter designated GVB) which is significantly higher than the control. Preferred MAS compounds are such having a percentage GVB of at least 50%, preferably at least 80%.

Examples of MAS compounds are mentioned in WO 96/00235, corresponding to U.S. Pat. No. 5,716,777, which describes, inter alia, sterol derivatives, WO 96/27658, corresponding to U.S. Pat. No. 5,830,757, which describes, inter alia, inhibitors of enzymes involved in the biosynthesis of cholesterol, for example, lanosterol 1.4 reductase, 4-demethylase, and lanosterol 8-7-isomerase, and endogenous meiosis activating substances, for example, FF-MAS and 4β-methylzymosterol, WO 97/00884, corresponding to U.S. patent application Ser. No. 08/973,661, which describes, inter alia, sterol derivatives, WO 98/28323, corresponding to U.S. patent application Ser. No. 09/333,391, which describes, inter alia, sterol derivatives, WO 98/52965, corresponding to U.S. Pat. No. 6,177,240, which describes, inter alia, 20-aralkyl-5α-pregnane derivatives, and WO 98/55498, corresponding to U.S. Pat. No. 6,262,282, which describes, inter alia, 17β-allyloxy(thio)alkyl-andostrane derivatives, more specifically in claim 1 thereof.

In WO 95/000265, some potential meiosis regulating substances were tested on immature female mice. 48 hours before the test animal were killed by cervical dislocation, they were given a single injection of human menopausal gonadotropin containing 20 IU FSH and 20 IU LH. The ovaries were removed, placed in a hypoxanthine medium and freed of extraneous tissue. Then, the oocytes were punctured out of the follicles, freed from cumulus cells and cultured in a medium containing a meiosis regulating derivative.

At present, in vitro maturation in humans has proven highly unsuccessful despite substantial interest and clinical efforts.

One object of the present invention is to treat human infertility.

Another object of the present invention is to improve the maturation of human oocytes.

Another object of the present invention is to improve the synchrony of nuclear, cytoplasmic and/or membranous oocyte maturation.

Another object of the present invention is to improve the fertility of oocytes.

Another object of the present invention is to improve the rate of implantation of oocytes by human in vitro maturation and fertilisation.

Another object of the present invention is to diminish the incidence of human preembryos with chromosome abnormalities (aneuploidy).

Another object of the present invention is to improve the cleavage rate of human preembryos.

Another object of the present invention is to improve the quality of human preembryos.

SUMMARY OF THIS INVENTION

It has now, surprisingly, been found that the IVF can be improved substantially when a MAS compound is added at the stage in the usual method of performing in vitro fertilisation where one would expect that the maturation had taken place in vivo.

Briefly, the present invention relates to a method for human in vitro fertilisation wherein a woman, within a consecutive period of 30 days, is treated with a hypothalamic hormone and/or a pituitary hormone or an agonist or antagonist thereof or an active derivative thereof where after oocytes are aspirated and actively final matured or the oocyte maturation is synchronised in vitro in contact with a MAS compound. Preferred embodiments of this invention are those stated in the sub claims below.

DETAILED DESCRIPTION OF THIS INVENTION

Referring to the female cycle, on way of performing the treatment of this invention is as follows:

Around day 21 in one cycle to around day 15 in the following cycle: The eggs are stimulated by treating the woman with GnRH, e.g. Synarel (400–600 µg per day).

Around days 6–15 in the second cycle: The eggs are stimulated by treating the woman with FSH, e.g. Gonal-F, Puregon or Humegon (150–400 IU per day).

Around days 15–16 in the second cycle: The eggs are stimulated by treating the woman with hCG, e.g. Pregnyl or Profasi (2000–5000 IU per day).

Around day 18 in the second cycle: The eggs are retrieved from the woman.

Around day 18–19 in the second cycle: The eggs are maturated with a MAS compound in order to stimulate the meiosis. In this additional maturation step, the concentration of MAS compound may be in the range about 0.1–100 µmol per liter, e.g. 10–20 µmol per liter. The time for this maturation step may be in the range around 1–60 hours. If the preovulatory follicles are induced to luthenise with a lutenising hormone or an agonist or antagonist thereof or an active derivative thereof and/or human chorion gonadotropins or an agonist or antagonist thereof or an active derivative thereof, the maturation of the oocytes with the MAS compound is for a duration of about 1–15 hours, preferably about 6 hours. If, however, preovulatory follicles are not induced to lutenise with a lutenising hormone or an agonist or antagonist thereof or an active derivative thereof and/or human chorion gonadotropins or an agonist or antagonist thereof or an active derivative thereof, the maturation of the oocytes with the MAS compound is for duration of about 15–60 hours.

Around days 19–21 in the second cycle: The eggs are fertilised in vitro.

From the day before aspiration, the woman will receive an oestrogen, e.g., oestrogen valerate (2×10 mg daily). Two days later, she will also receive a progestogen, e.g., Progestane vagetoria, daily, which will render the lining of the uterus more prone to receive the future embryos. The duration of this treatment will be individually designed per patient. The doctor can chose among a variety of oestrogens and progestogens.

Around day 21 in the second cycle: One or more embryos are transferred to the woman's uterus.

The description above is designated MAS add-on to the existing IVF protocol to improve efficacy by mediating a final or complete maturation or synchrony in the oocyte. Alternatively, MAS can be used to rescue oocytes in cycles that otherwise would be cancelled due to apparent FSH hyper response. In this instance, the responsible clinician would consider cancellation based on the estradiol profile, ultra-sonography (PCO like response) thus avoiding the hCG treatment. The oocytes are aspirated at the time around day 15–16 substituting hCG treatment.

Apart from the additional maturation step with a MAS compound, the above IVF is performed the usual way. Since one expects that by the traditional IVF procedure the eggs had been matured sufficiently, one would not expect that it would have any additional effect to add this additional maturation step.

Most of the steps in the above treatment and procedure are performed in a known manner and the remaining steps are performed in a manner known per se. More details about the removal of the oocytes from follicles in the ovary, culturing of the isolated oocytes, the culture medium to be used, the fertilisation with sperm, and the transfer of the embryo to the fallopian tube can be found in the literature, for example, in U.S. Pat. No. 5,693,534 which is hereby incorporated by reference.

According to this invention, the MAS compound is added to the culture medium used. In this medium, the amount of the MAS compound is in the range from about 0.01 to about 100 µM, preferably in the range from about 0.1 to about 100 µM.

A preferred reason for treating a woman, within a consecutive period of 30 days, with a hypothalamic hormone and/or a pituitary hormone or an agonist or antagonist thereof or an active derivative is to obtain multiple preovulatory follicles.

Hypothalamic hormones are hormones present in the human hypothalamus. Pituitary hormones are hormones present in the human pituitary gland. Gonadotropic hormones are hormones secreted by the anterior lobe of the pituitary in vertebras and by mammalian placenta, which control the activity of gonads. Chemically, they are glycoproteins. Examples of gonadotropic hormones are FSH, LH and chorion gonadotropin, e.g. human chorion gonadotropin (hereinafter designated hCG). FSH stimulates growth of ovarian follicles and their oocytes in ovary and the formation of spermatozoa in testis. FSH can, e.g., be menopausal FSH or recombinant FSH. In females, LH activates the oestrogen-producing tissue of the ovaries to produce progesterone, probably promotes the final stages of the development of ovarian follicles, initiates the final oocyte maturation, induces ovulation and in mammals initiates corpus luteum development. These hormones are known. It is obvious for the skilled art worker that, alternatively, agonists or antagonists of these hormones can be used. It is also obvious for the skilled art worker that, alternatively, active analogues of these hormones can be used. Some of these agonists, antagonists and analogues are known and other can be prepared by process known per se. Examples of such known processes are chemical synthesis and genetic engineering.

In a preferred embodiment, the present invention relates to a method or use wherein the consecutive period of 30 days within which the woman is treated with a hypothalamic hormone and/or a pituitary hormone or an agonist or antagonist thereof or an active derivative thereof is at least about 7 days, preferably at least about 10 days, more preferred at least about 14 days.

In another preferred embodiment, the present invention relates to a method or use wherein the woman is treated for infertility, and/or for improving the maturation of her oocytes, and/or for improving the synchrony of nuclear, cytoplasmic and/or membranous oocyte maturation, and/or for improving the fertility of her oocytes, and/or for improving the rate of implantation by human in vitro maturation and fertilisation In another preferred embodiment, the present invention relates to a method or use wherein the consecutive period is one menstrual cycle.

In another preferred embodiment, the present invention relates to a method or use wherein the maturation of the oocytes with the MAS compound is for a duration of about 15 to about 60 hours.

In another preferred embodiment, the present invention relates to a method or use wherein preovulatory follicles are induced to lutenise with a luteinising hormone (LH) or an agonist or antagonist thereof or an active derivative thereof and/or human chorion gonadotropin (HCG) or an agonist or antagonist thereof or an active derivative thereof.

In another preferred embodiment, the present invention relates to a method or use wherein the maturation of the oocytes with the MAS compound is for a duration of about 1 to about 15 hours, preferably about 6 hours.

In another preferred embodiment, the present invention relates to a method or use wherein the dosage of MAS compound used is about 0.01 to about 100 μmol per liter, preferably about 0.1 to about 100 μmol per liter.

In another preferred embodiment, the present invention relates to a method or use wherein the MAS compound is one of the compounds mentioned in WO 96/00235 (corresponding to U.S. Pat. No. 5,716,777), WO 96/27658 (corresponding to U.S. Pat. No. 5,830,757), WO 97/00884 (corresponding to U.S. patent application Ser. No. 08/973, 661), WO 98/28323 (corresponding to U.S. patent application Ser. No. 09/333,391), WO 98/52965 (corresponding to U.S. Pat. No. 6,177,240) and WO 98/55498 (corresponding to U.S. Pat. No. 6,262,282), more specifically compounds mentioned in claim 1 thereof.

In another preferred embodiment, the present invention relates to a method or use wherein the MAS compound is FF-MAS.

Additionally, the present invention relates to the use of a hypothalamic hormone and/or a pituitary hormone or an agonist or antagonist thereof or an active derivative thereof in the manufacture of a hormone product which is to be administered to a woman who, within a consecutive period of 30 days, is treated with a hypothalamic hormone and/or a pituitary hormone or an agonist or antagonist thereof or an active derivative thereof, and from whom, immediately after said period, one or more oocytes are aspirated, where after said oocyte(s) is/are cultivated in a convenient medium containing a MAS compound as defined herein, where after said oocyte(s) is/are fertilised with human sperm, and where after the resulting embryo(s) is/are transferred to a woman.

Additionally, the present invention relates to the use of a hypothalamic hormone and/or a pituitary hormone or an agonist or antagonist thereof or an active derivative thereof and of a MAS compound for the manufacture of a medicament for the treatment of human in vitro fertilisation wherein a hypothalamic hormone and/or a pituitary hormone or an agonist or antagonist thereof or an active derivative thereof is, within a consecutive period of 30 days, used to treat a women and, thereafter, the MAS compound is used in an in vitro oocyte maturation of the egg or eggs retrieved from this woman.

Additionally, the present invention relates to a pharmaceutically kit in unit dosage form for use by in vitro fertilisation comprising separate unit dosages, said kit comprising separate dosage units for sequential daily administration of a hypothalamic hormone and/or a pituitary hormone or an agonist or antagonist thereof or an active derivative thereof for sequential daily administration and 1 dosage units of a MAS compound. This kit may have the preferred features described above.

The present invention is further illustrated by the following examples, which, however, are not to be construed as limiting. The features disclosed in the foregoing description, in the following examples and in the claims may, both separately and in any combination thereof be material for realising the invention in diverse forms thereof.

EXAMPLE 1

Method Used for Electing MAS Compounds

Oocytes were obtained from immature female mice (C57BL/6J×DBA/2J F1, Bomholtgaard, Denmark) weighing 13–16 grams, that were kept under controlled temperature (20–22° C.), light (lights on 06.00–18.00) and relative humidity (50–70%). The mice received an intra-peritoneal injection of 0.2 ml gonadotropins (Gonal-F, Serono) containing 20 IU FSH and 48 hours later the animals were killed by cervical dislocation. The ovaries were dissected out and the oocytes were isolated in Hx-medium (see below) under a stereomicroscope by manual rupture of the follicles using a pair of 27 gauge needles. Spherical oocytes displaying an intact germinal vesicle (hereinafter designated GV) were divided in cumulus enclosed oocytes (hereinafter designated CEO) and naked oocytes (hereinafter designated NO) and placed in α-minimum essential medium (α-MEM without ribonucleosides, Gibco BRL, Cat. No. 22561) supplemented with 3 mg/ml bovine serum albumin (BSA, Sigma Cat. No. A-7030), 5 mg/ml human serum albumin (HSA, Statens Seruminstitut, Denmark), 0.23 mM pyruvate (Sigma, Cat. No S-8636), 2 mM glutamine (Flow Cat. No. 16-801), 100 IU/ml penicillin and 100 μg/ml streptomycin (Flow, Cat No. 16-700). This medium was supplemented with 3 mM hypoxanthine (Sigma Cat. No. H-9377) and designated Hx-medium.

The oocytes were rinsed three times in Hx-medium and oocytes of uniform size were divided into groups of CEO and NO. CEO and NO were cultured in 4-well multidishes (Nunclon, Denmark) in which each well contained 0.4 ml of Hx-medium and the compound to be tested in a concentration of 10 μM. One control well (i.e., 35–45 oocytes cultured in identical medium with no addition of test compound) was always cultured simultaneously with 3 test wells (35–45 oocytes per well supplemented with test compound).

The oocytes were cultured in a humidified atmosphere of 5% $CO_2$ in air for 24 hours at 37° C. By the end of the culture period, the number of oocytes with GV, GVB and polar bodies (hereinafter designated PB), respectively, were counted using a stereo microscope (Wildt, Leica MZ 12). The percentage of GVB, defined as percentage of oocytes undergoing GVB per total number of oocytes in that well, was calculated as:

%GVB=((number of GVB+number of PB)/total number of oocytes)×100.

EXAMPLE 2

Procedure

All IVF patients can potentially receive this treatment, age range 20 to 45 year. The hormonal treatment can be a short or long gonadotropin based treatment with or without pituitary down regulation or with and without the use of GNRH antagonist and with or without the use of hCG. Future appropriate hormonal therapies designed for IVF can also be used. Medium to full size follicles (size 10 to 25 mm, preferential 16 to 20 mm follicles) will be aspirated under ultrasound guidance.

The aspirated fluid will be searched for cumulus oocytes complexes (COC) and once identified under the stereomicroscope (with or without the use of embryo filters), the COC will be placed in culture.

The exposure to FF-MAS can vary from 1 to 60 hours, preferentially from 4 to 30 hours, and can be before, under and up to 24 hours after fertilisation. A wide variety of oocyte culture media or media components known to the skilled worker can be used. Human serum albumin (HSA) may or may not be added to the medium. If added, it can be in a concentration of 0.1 to 100 mg/ml, preferentially 5 to 15 mg/ml or 0.5 to 1.5% volume/volume. The formulation of FF-MAS may be in the form of an ethanol stock solution, DMSO or other organic solvent solution or it may be in form of FF-MAS/HSA dry coated wells ready to use just by adding the appropriate culture medium. The concentration of FF-MAS may vary from 0.1 $\mu$M to 100 $\mu$M, preferentially 10 to 30 $\mu$M.

Following or during in vitro culture with FF-MAS, the oocytes may be fertilised by conventional IVF or by intracytoplasmatic sperm injection (ICSI) or by future appropriate fertilisation methods leading to fertilised zygotes. The developing embryo may be transferred on day 1 to day 6 after fertilisation, preferentially on day 2 to 3, either as single egg transfer or multiple egg transfer.

The patient can receive progesterone and/or oestrogen therapy before and after the egg transfer in individually designed protocols to prime and sustain appropriate receptive endometrial lineage.

Compared with the know procedures, better results were obtained using the above procedure.

EXAMPLE 3

Use of FF-MAS as Adjunct to a Standard FSH Based IVF Treatment

The patient underwent down regulation with recombinant FSH with an average daily dose of 225 IU starting on Day 1 or 2 of the current cycle and used a GnRH antagonist, i.e., Cetrorelix (1 mg daily, subcutaneously, one shot), in the current cycle. At least 3 follicles of 17 mm or more were present at the time of administering hCG, i.e., Profasi (10.000 IU, one shot). Follicles were aspirated and metaphase II oocytes were cultured in oocyte culture system containing standard in vitro fertilization (IVF) media (IVF 20 (which is available from Scandinavian IVF Science AB, Gothenburg, Sweden)) supplemented with human serum albumin (0.8%) and FF-MAS (5 $\mu$M). All oocytes were cultured under normal conditions at 37° C. in the incubator. Each oocyte was cultured in one well in a four-chamber culture dish as culture media system. The duration of exposure to the culture media with treatment was 4 hours (±30 minutes) before intracytoplasmic sperm injection (hereinafter designated ICSI) and 20 hours (±1 hour) after ICSI in the above IVF 20 medium. Preembryos were evaluated for cleavage stage and fragmentation/morphology at 1, 2 and 3 days post ICSI. After 3 days of culture, a selection of the best preembryos, typically two preembryos, was replaced to the female patient. The female patient received an estrogen, i.e., Estrofem (6 mg/daily), and a progesterone, i.e. Utrogestan (600 mg/daily, micronized, vaginal suppository), to render the endometrium lining the patient uterus responsive and ready for allowing implantation of the transferred eggs. The continuation of supporting steroid hormones was patient depending and was seponated after 3–10 weeks depending on ultrasound scans and blood testing.

Compared with the know procedures, better results were obtained using the above procedure.

EXAMPLE 4

Use of FF-MAS as Adjunct to a Standard FSH Based IVF Treatment

The patient underwent down regulation with an GnRH analog, i.e., Synarel (nasal spray, two puffs daily), for at least 14 days (starting in the luteal phase of the previous cycle or Day 1 or 2 in the follicular phase of the current cycle) and ovarian stimulation with recombinant FSH with an average daily dose of 225 IU. At least 3 follicles of 17 mm or more were present at the time of administering hCG, i.e. Profase (10.000 IU, one shot). Follicles were aspirated and metaphase II oocytes were cultured in oocyte culture system containing standard in vitro fertilization (IVF) media (IVF 20 (which is available from Scandinavian IVF Science AB, Gothenburg, Sweden)) supplemented with human serum albumin (0.8%) and FF-MAS (5 $\mu$M). All oocytes were cultured under normal conditions at 37° C. in the incubator. Each oocyte was cultured in one well in a four-chamber culture dish as culture media system. The duration of exposure to the culture media with treatment was 4 hours (±30 minutes) before intracytoplasmic sperm injection (ICSI) and 20 hours (±1 hour) after ICSI in the above IVF 20 medium. Preembryos were evaluated for cleavage stage and fragmentation/morphology at 1, 2 and 3 days post ICSI. After 3 days of culture, a selection of the best preembryos, typically two preembryos, was replaced to the female patient. The female patient received an estrogen, i.e., Estrofem (6 mg/daily), and a progesterone, i.e., Utrogestan (600 mg/daily, micronized, vaginal suppository), daily to render the endometrium lining the patient uterus responsive and ready for allowing implantation of the transferred eggs. The continuation of supporting steroid hormones was patient depending and was seponated after 3–10 weeks depending on ultrasound scans and blood testing.

Compared with the know procedures, better results were obtained using the above procedure.

EXAMPLE 5

Using the procedure described in Example 3 with the proviso that in stead of using FF-MAS in a concentration of 5 $\mu$M, FF-MAS was used in a concentration of 20 $\mu$M, better results were obtained than with the know procedures.

EXAMPLE 6

Using the procedure described in Example 4 with the proviso that in stead of using FF-MAS in a concentration of 5 $\mu$M, FF-MAS was used in a concentration of 20 $\mu$M, better results were obtained than with the know procedures.

What is claimed is:

1. A method for in vitro fertilization of human oocytes, said method comprising:
   (a) treating a female patient within a consecutive period of 30 days with a hypothalamic hormone, alone or in combination with a pituitary hormone, or an agonist or antagonist thereof, or a pituitary hormone or an agonist or antagonist thereof alone;

(b) retrieving an oocyte(s) from the patient;
(c) maturing the oocyte(s) in vitro, wherein during said maturation the oocyte(s) are exposed to a meiosis activating substance (MAS), and wherein the meiosis activating substance is a compound having a percentage germinal vesicle breakdown which is significantly higher than a control; and
(d) fertilizing the in vitro matured oocyte(s).

2. The method according to claim 1 wherein the consecutive period within which the woman is treated with a hypothalamic hormone, alone or in combination with pituitary hormone or an agonist or antagonist thereof, or a pituitary hormone or an agonist or antagonist thereof alone, is at least about 7 days.

3. The method according to claim 1 wherein the consecutive period is one menstrual cycle.

4. The method according to claim 1 wherein the maturation of the oocytes with the meiosis activating substance (MAS) compound is for a duration of about 15 hours to about 60 hours.

5. The method according to claim 1 wherein step (a) of said method comprises inducing preovulatory follicles to luteinise with a luteinising hormone (LH) or an agonist or antagonist thereof alone or in combination with human chorion gonadotropin (HCG) or an agonist or antagonist thereof, or a human chorion gonadotropin (HCG) or an agonist or antagonist thereof.

6. The method according to claim 5 wherein the maturation of the oocytes with the meiosis activating substance (MAS) compound is for a duration of about 1 to about 15 hours.

7. The method according to claim 1 wherein the dosage of the meiosis activating substance (MAS) compound is about 0.01 to about 100 µmol per liter.

8. The method according to claim 1 wherein the meiosis activating substance (MAS) compound is 4,4-dimethyl-5α-cholesta-8,14,24-triene-3β-ol.

9. The method according to claim 1, wherein the meiosis activating substance (MAS) compound has a percentage germinal vesicle breakdown at least 50% higher than the control.

10. The method according to claim 1 wherein the consecutive period within which the woman is treated with a hypothalamic hormone, alone or in combination with pituitary hormone or an agonist or antagonist thereof, or a pituitary hormone or an agonist or antagonist thereof alone, is at least about 14 days.

11. The method according to claim 1 wherein the maturation of the oocytes with the meiosis activating substance (MAS) compound is for a duration of about 1 to about 15 hours.

12. The method according to claim 1 wherein the maturation of the oocytes with the meiosis activating substance (MAS) compound is for a duration of about 1 to about 6 hours.

13. The method according to claim 1, wherein the meiosis activating substance (MAS) compound is selected from the group consisting of sterol derivatives, inhibitors of enzymes involved in the biosynthesis of cholesterol, endogenous meiosis activating substances, 20-aralkyl-5α-pregnane derivatives, or a 17β-allyloxy(thio)alkyl-andostrane derivative.

14. A pharmaceutical kit comprising in unit dosage form for in vitro fertilization, separate dosage units for sequential daily administration of a hypothalamic hormone, alone or in combination with a pituitary hormone or an agonist or antagonist thereof, or a pituitary hormone or an agonist or antagonist thereof alone, and 1 dosage unit of a meiosis activating substance (MAS) compound.

15. A method for treating a female patient for infertility, for improving the maturation of her oocytes, for improving the synchrony of nuclear, cytoplasmic or membraneous oocyte maturation, for improving the fertility of her oocytes, or for improving the rate of implantation by human in vitro maturation and fertilization, said method comprising:
(a) treating the female patient within a consecutive period of 30 days with a hypothalamic hormone, alone or in combination with a pituitary hormone, or an agonist or antagonist, or a pituitary hormone or an agonist or antagonist thereof alone;
(b) retrieving an oocyte(s) from the patient;
(c) maturing the oocyte(s) in vitro, wherein during said maturation the oocyte(s) are exposed to a meiosis activating substance (MAS), and wherein the meiosis activating substance is a compound having a percentage germinal vesicle breakdown which is significantly higher than a control; and
(d) fertilizing the in vitro matured oocyte(s).

* * * * *